United States Patent
Zhu

(10) Patent No.: US 10,937,208 B2
(45) Date of Patent: Mar. 2, 2021

(54) PET IMAGE RECONSTRUCTION AND PROCESSING USING LESION PROXIES

(71) Applicant: KONINKLIJKE PHILIPS N.V., Eindhoven (NL)

(72) Inventor: Yang-Ming Zhu, Solon, OH (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 388 days.

(21) Appl. No.: 15/774,372

(22) PCT Filed: Nov. 8, 2016

(86) PCT No.: PCT/IB2016/056700
§ 371 (c)(1),
(2) Date: May 8, 2018

(87) PCT Pub. No.: WO2017/085587
PCT Pub. Date: May 26, 2017

(65) Prior Publication Data
US 2020/0258271 A1 Aug. 13, 2020

Related U.S. Application Data

(60) Provisional application No. 62/257,760, filed on Nov. 20, 2015.

(51) Int. Cl.
*G06K 9/00* (2006.01)
*G06T 11/00* (2006.01)
(Continued)

(52) U.S. Cl.
CPC .......... *G06T 11/006* (2013.01); *G06F 3/0482* (2013.01); *G06F 3/0483* (2013.01);
(Continued)

(58) Field of Classification Search
None
See application file for complete search history.

(56) References Cited

U.S. PATENT DOCUMENTS

| 2009/0247847 | A1 | 10/2009 | Pogue |
| 2009/0273610 | A1* | 11/2009 | Busch ............ G06T 5/003 345/619 |
| 2013/0105699 | A1* | 5/2013 | Asma ............ A61B 6/488 250/363.03 |

(Continued)

FOREIGN PATENT DOCUMENTS

| EP | 2360643 | 8/2011 |
| WO | 2006117706 | 11/2006 |

OTHER PUBLICATIONS

Wangerin, et al., "Improving lesion detectability in PET imaging with a penalized likelihood reconstruction algorithm"; Progress in Biomedical Optics and Imaging, SPIE, vol. 9416, May 17, 2015.
(Continued)

*Primary Examiner* — Atiba O Fitzpatrick

(57) ABSTRACT

When performing nuclear medicine image reconstruction, lesion proxies (208) are introduced by a clinician and merged with real acquired scan data outside or inside the patient in the patient image. By monitoring the image attributes of the lesion proxies during reconstruction and processing, reconstruction and processing parameters can be dynamically adapted or adjusted in order to optimize image quality and quantitation to improve delivery of precise, personalized medical treatment.

12 Claims, 3 Drawing Sheets

(51) Int. Cl.
  *G16H 30/20* (2018.01)
  *G16H 30/40* (2018.01)
  *G06F 3/0482* (2013.01)
  *G06F 3/0483* (2013.01)
  *G06F 3/0484* (2013.01)
  *G06T 5/00* (2006.01)
  *G06T 7/00* (2017.01)

(52) U.S. Cl.
  CPC .......... *G06F 3/04847* (2013.01); *G06T 5/005* (2013.01); *G06T 7/0014* (2013.01); *G06T 11/008* (2013.01); *G16H 30/20* (2018.01); *G16H 30/40* (2018.01); *G06T 2200/24* (2013.01); *G06T 2207/10081* (2013.01); *G06T 2207/10088* (2013.01); *G06T 2207/10104* (2013.01); *G06T 2207/10108* (2013.01); *G06T 2207/30096* (2013.01); *G06T 2207/30168* (2013.01); *G06T 2211/424* (2013.01)

(56) References Cited

U.S. PATENT DOCUMENTS

| | | | | |
|---|---|---|---|---|
| 2013/0136328 | A1* | 5/2013 | Jansen | G06T 11/005 |
| | | | | 382/131 |
| 2014/0126794 | A1* | 5/2014 | Ahn | G06T 11/008 |
| | | | | 382/131 |
| 2015/0146845 | A1 | 5/2015 | Thibault | |
| 2017/0053423 | A1* | 2/2017 | Ahn | A61B 6/037 |

OTHER PUBLICATIONS

D'Alessandro, et al., "Synthetic Positron Emission Tomography-Computed Tomography Images for Use in Perceptual Studies", Seminars in Nuclear Medicine; vol. 41, No. 6, Nov. 2011.

Tanyi, et al., "Phantom investigation of 3D motion-dependent volume aliasing during CT simulation for radiation therapy planning"; Radiation Oncology 2007.

* cited by examiner

PET IMAGE RECONSTRUCTION AND PROCESSING USING LESION PROXIES

CROSS REFERENCE TO RELATED APPLICATIONS

This application is the U.S. National Phase application under 35 U.S.C. § 371 of International Application No. PCT/IB2016/056700, filed Nov. 8, 2016, published as WO 2017/085587 on May 26, 2017, which claims the benefit of U.S. Provisional Patent Application No. 62/257,760 filed Nov. 20, 2015. These applications are hereby incorporated by reference herein.

FIELD

The present invention finds application in nuclear medicine imaging reconstruction systems and methods. However, it will be appreciated that the described techniques may also find application in other imaging systems, other reconstruction techniques, and the like.

BACKGROUND

In conventional PET reconstruction and post-processing systems, a "one size fits all" approach is taken, where the same set of parameters is used during PET reconstruction and post-processing, regardless the differences in acquisition condition, patient demographics and disease history, etc. Once the parameters are chosen, they are uniformly applied to all patients under all conditions.

PET reconstruction typically employs statistical, iterative algorithms, e.g. the OSEM (ordered-subset expectation maximization) and its variants. In the OSEM algorithms, the number of iterations is a key parameter and it is chosen empirically, and once chosen, it is fixed. Post-reconstruction image processing such as resolution recovery or low-pass filtering is often exploited to improve the image quality. These post-filtering algorithms have various parameters, e.g. a point spread function (PSF) has a noise regularization parameter to moderate noise propagation. These parameters are empirically chosen and fixed afterwards.

To improve patient care, personalized medicine and precision medicine are often cited by physicians as critical to their practice. Personalized and precision medicine represents a trend in medical decision making, practice, and product offerings. To deliver personalized medicine with precision, it is highly desirable to adaptively change the above-mentioned parameters on a per-patient basis, per study, and per organ or region. However, the ground truth of patient, study, and/or region is not known a priori, which makes it hard if not impossible to adapt these parameters in practice.

The present application provides new and improved systems and methods that facilitate using lesion proxies to optimize reconstruction settings for reconstructing nuclear medicine images, thereby overcoming the above-referenced problems and others.

SUMMARY

In accordance with one aspect, a system that facilitates reconstructing a nuclear medicine image using lesion proxies comprises a PET scanner that acquires scan data of the patient, a graphical user interface (GUI) that receives parameter information describing one or more lesion proxies for positioning in a nuclear medicine image of a patient, and an event simulation module that simulates the radioactive decay and other physical processes such as attenuation and scattering of the one or more lesion proxies. The system further comprises a reconstruction processor that merges lesion proxy simulation data with the acquired scan data, monitors image attributes of lesion proxies, adjusts one or more reconstruction parameters as a function of lesion proxy status, and iteratively reconstructs the nuclear medicine image using one or more adjusted reconstruction parameters.

According to another aspect, a method for reconstructing a nuclear medicine image using lesion proxies to improve image quality comprises acquiring patient scan data, reconstructing a first image of a region of interest (which may comprise the whole patient or a portion thereof) of the patient from the acquired scan data, receiving information regarding placement of one or more lesion proxies (208), which have known attributes, into the image, and simulating lesion proxy data describing radioactive decay, annihilation event, and other physical processes of the one or more lesion proxies. The method further comprises combining the simulated lesion proxy data with the acquired patient scan data, iteratively reconstructing the combined patient scan data and simulated lesion proxy data into at least a second image, monitoring one or more attributes of the one or more lesion proxies after each reconstruction, and adjusting reconstruction parameters after each reconstruction iteration as a function of the one or more monitored attributes.

According to another aspect, a graphical user interface (GUI) that facilitates generating a nuclear medicine image using lesion proxies comprises an image panel in which a patient image is presented to a user, a plurality of selectable and adjustable lesion proxy parameter tabs, and proxy menu from which predetermined lesion proxies can be selected. The GUI further comprises a proxy toggle tab that, when selected, toggles between a final patient image that includes the lesion proxies and a clean final patient image that does not include the lesion proxies.

Still further advantages of the subject innovation will be appreciated by those of ordinary skill in the art upon reading and understand the following detailed description.

BRIEF DESCRIPTION OF THE DRAWINGS

The drawings are only for purposes of illustrating various aspects and are not to be construed as limiting.

DETAILED DESCRIPTION

Conventional PET reconstruction systems are not adaptive to the patient and the patient's condition because there is no information provided to enable the systems to make decisions and thus adapt the behavior of reconstruction and processing. The described systems and methods overcome the above-mentioned problems by providing lesion proxies purposely introduced and merged to the acquired data. Since the ground truth of those lesion proxies is known, by monitoring the image attributes of the lesion proxies, the reconstruction and post-processing algorithms can self-adjust and adapt their parameters and behavior to generate optimal results.

The herein-described systems and methods facilitate adapting reconstruction and processing parameters for optimal image quality and quantitation per patient, per study, and per organ/region, as well as reporting the quantitation accuracy such as standardized uptake value (SUV) based on lesion proxies so that clinicians can put more confidence on other quantitative results the recon systems provide. These systems and methods also facilitate allowing clinicians to specify the desired image quality and quantitation levels differently for different regions, and placing lesion proxies close to the real lesion found during image review, in order to reconstruct and process the data again for further analysis of the real lesion. The clinicians can then infer the lesion characteristics based on the characteristics of lesion proxies.

Figure 1:
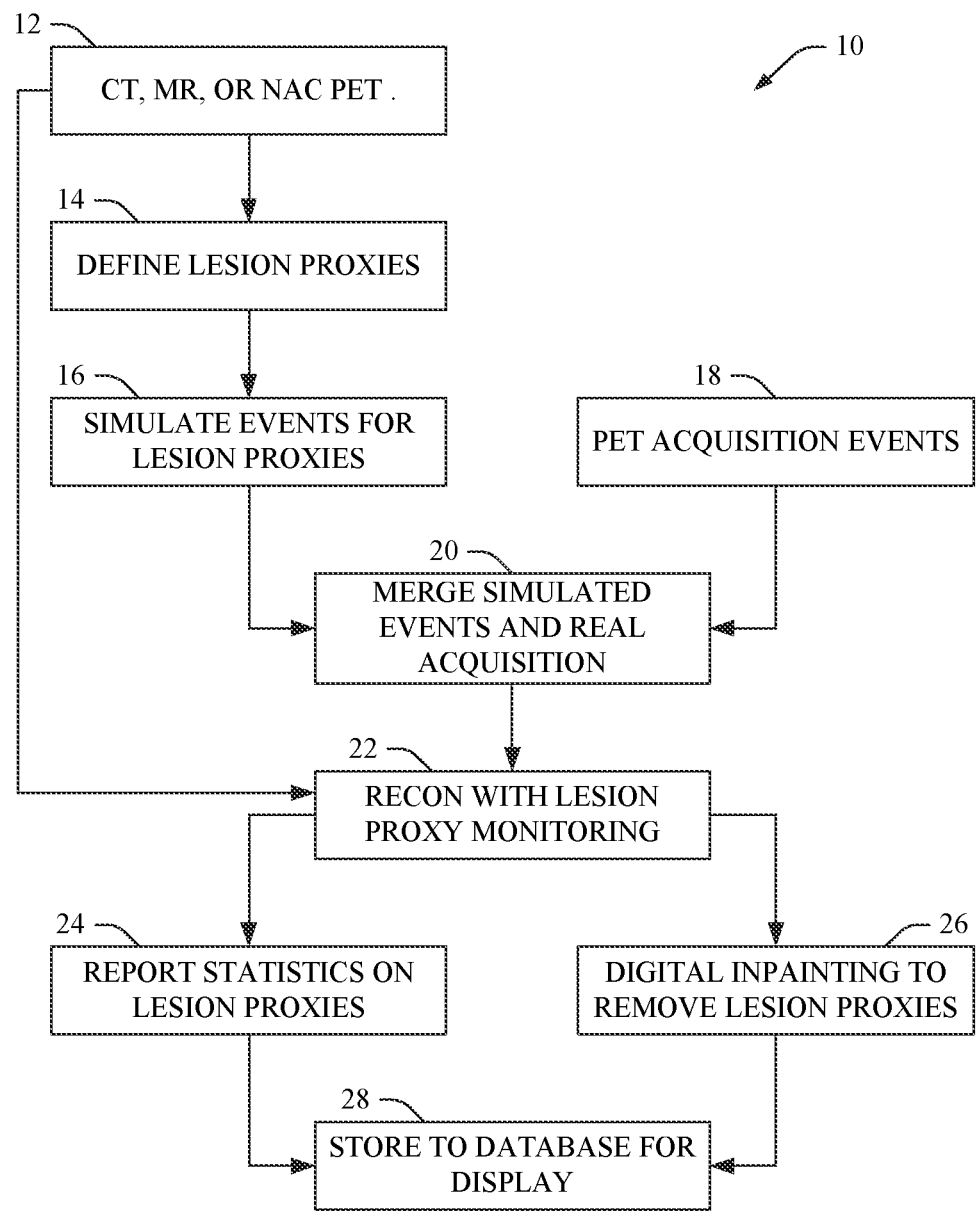
FIG. 1 illustrates a flow diagram that shows a method for reconstructing a nuclear medicine image using lesion proxies to improve image quality, in accordance with various features described herein.

FIG. 1 illustrates a flow diagram 10 that shows a method for reconstructing a nuclear medicine image using lesion proxies to improve image quality, in accordance with various features described herein. At 12, patient image data is acquired. The scan data can be, e.g., computed tomography (CT) image data, magnetic resonance (MR) image data, positron emission tomography (PET) image data, non-attenuation corrected PET (NAC PET) image data, single photon emission computed tomography (SPECT) image data, combinations of the foregoing such as PET/CT, PET/MR, SPECT/CT, or the like. The remainder of this application will discuss PET-related modalities. For instance, when defining a lesion proxy, the CT data in the CT/PET scan, the MR in the MR/PET scan, or the NAC PET for the same PET study (which is typically created during the PET study) can be used to aid lesion proxy definition. Additionally, the NAC PET data can be used to define the lesion proxy in a standalone PET scenario.

At 14, lesion proxies are placed on the CT, MR, or NAC PET (e.g., by a clinician via a graphical user interface (GUI), automatically, or the like). The lesion proxies are used to simulate events (e.g., radioactive decay, annihilation events with scattering, attenuation, etc.) that would be caused by an actual lesion having the characteristics of the lesion proxy, at 16. The result of the simulation is raw data. Actual patient PET event acquisition is performed at 18. At 20, the acquired PET events are merged with the simulated proxy events.

At 22, the real and simulated events are reconstructed and the lesion proxies are monitored to evaluate their image quality and quantitation attributes, which are used as the proxies to the true lesions in the reconstructed or processed images. For instance, a standardized uptake value (SUV) of the lesion proxies in the reconstructed image can be monitored and compared to the known SUV associated with the lesion proxies. Reconstruction and processing parameters are dynamically adjusted until the monitored attributes (e.g., SUV or the like) matches or substantially matches the known attribute value, in order to achieve optimal results. In one embodiment, where multiple lesion proxies are used, the SUV values of all lesion proxies are used to adjust reconstruction parameters. At 24, a statistical report is made on the lesion proxies so that clinicians can infer the image quality and quantitation of the reconstruction and processing the system provides. At 26, the introduced lesion proxies are digitally removed using, e.g., image inpainting techniques to generate a clean image. At 28, the statistical reports and clean image(s) are stored to memory for display (e.g., via the GUI) to a clinician.

According to an example, nuclear scan data of a patient is acquired and reconstructed into a patient image. In the case of PET/CT, the CT image is displayed to a clinician on a GUI, and the clinician defines and/or inserts one or more lesion proxies into the image at desired locations. The lesion proxies can have a predefined size, shape, activity distribution, or other predefined characteristics. In another embodiment, the lesion proxies are individually designed to have specific values for the foregoing parameters. In either case, the lesion proxies, having known attributes, are inserted into the patient image. A reconstruction processor merges the patient scan data with the simulated lesion proxy data and iteratively reconstructs the combined data. Periodically (e.g., after each N iterations, where N is an integer), statistical data regarding the lesion proxies is calculated and stored. One example of statistical data that can be monitored is the standardized uptake value (SUV) of the reconstructed lesion proxies. Reconstruction parameters are adjusted until the SUV of the lesion proxies in the image matches a known SUV for the lesion proxies (i.e., a SUV pre-associated during lesion proxy definition). Once the SUV in the reconstructed image matches the pre-associated or known SUV, reconstruction iteration is terminated and the optimized reconstruction parameters or settings are stored to memory. A clean final image can then be generated without lesion proxies using the stored reconstruction parameters or settings. In another embodiment, the lesion proxies are removed using a digital inpainting technique (e.g., without performing a separate reconstruction without lesion proxies). The monitored statistical data is not limited to SUV data, but may be, for example, counts, activity concentration, etc. In another embodiment, the statistical data can comprise information related to the uniformity of the data (e.g., in cases where the lesion proxy is intended to be uniform). In one embodiment, the systems and methods described herein are employed to optimize reconstruction of nuclear medicine images in which motion is present. For instance, a dynamic model can be constructed (e.g., using gating techniques or the like) to simulate lesion proxy events during the course of a dynamic sequence (e.g., cardiac cycle, respiratory cycle, etc.) Kinetic model parameters can be derived and compare to "set" values (e.g., distribution and confidence level, or the like). For respiratory gating studies, organ motion derived from the lesion proxy can be compared to an actual "set" motion profile, and the statistics of the difference are computed, etc.

Figure 2:
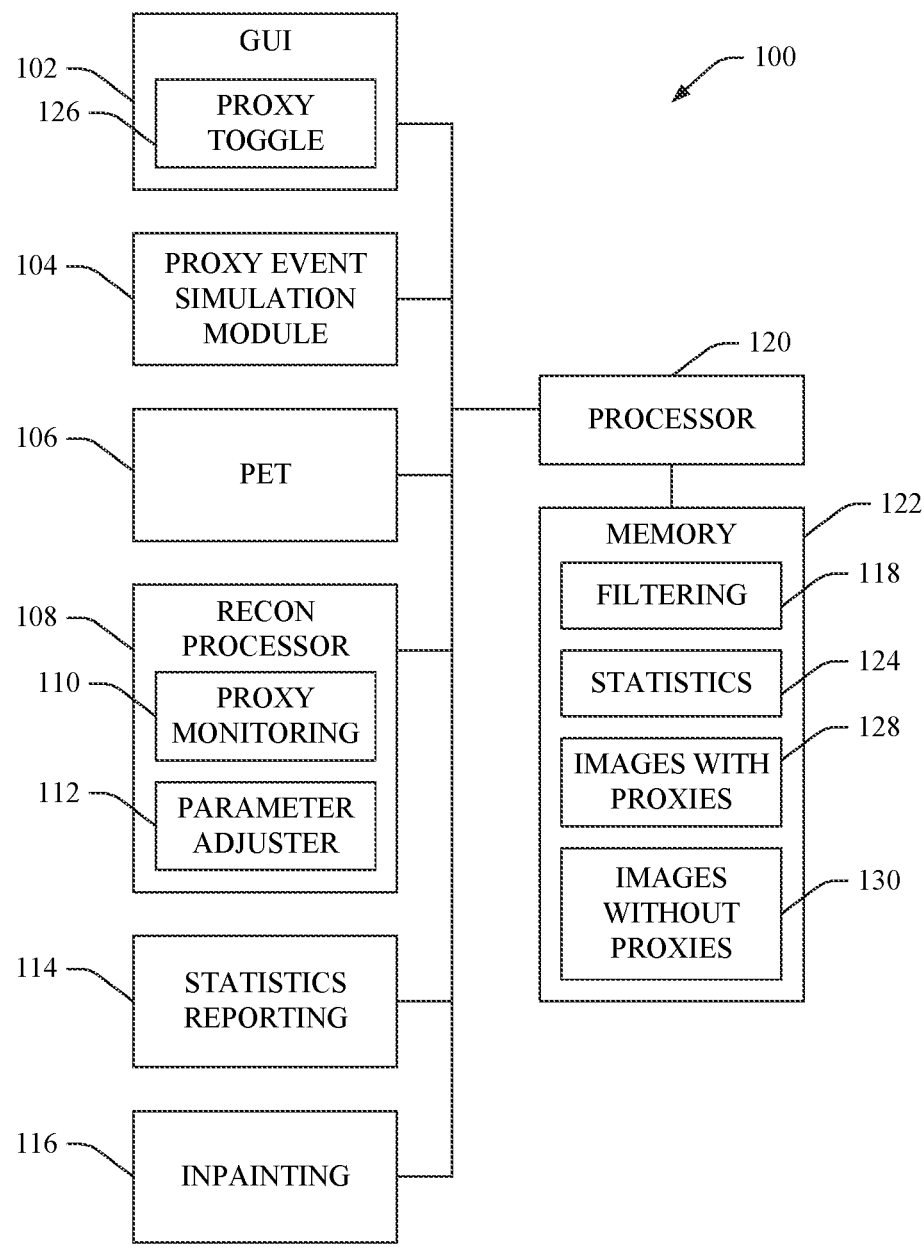
FIG. 2 illustrates a system that facilitates reconstructing a nuclear medicine image using lesion proxies to improve image quality, in accordance with one or more features described herein.

FIG. 2 illustrates a system 100 that facilitates reconstructing a nuclear medicine image using lesion proxies to improve image quality, in accordance with one or more features described herein. The system comprises a graphical user interface (GUI) 102 that allows a clinician to specify the lesion proxies, their locations, shapes and sizes, and activity distributions. In one embodiment, one or more lesion proxies is placed automatically as a function of one or more parameters, which may comprise, e.g., patient size, the type of study or protocol being performed, or the like. In another embodiment, the system provides recommendations or suggestions to the clinician based on the one or more parameters. For instance, a processor 120 can evaluate the one or more parameters and suggest one or more of proxy size, shape, type, and position to the clinician for confirmation.

The system further comprises an event simulation module 104 that simulates the radioactive decay and annihilation events of one or more lesion proxies as if detected by an acquisition system, and a PET scanner 106 that acquires real scan data of the patient. A modified reconstruction processor 108 is provided that comprises a lesion proxy monitor 110 that monitors the image attributes of lesion proxies, and a reconstruction parameter adjustment module 112 that adjusts reconstruction parameters as a function of lesion proxy status. The system further comprises a statistical reporting tool 114 that reports the image characteristics of lesion proxies after recon and processing are complete. A digital inpainting tool 116 is also provided, which segments out the lesion proxies and replaces them with proper backgrounds once the lesion proxies are no longer desired.

The GUI 102 allows clinicians to define lesion proxies, including their location, shape, size, and activity distribution in image space. The characteristics of the lesion proxies can be tailored to diagnostic needs and according to physician preference. The lesion proxies can be placed outside the patient body or within the body in the image. In one embodiment, 3D GUI tools are provided so that the clinicians can navigate through the 3D space with ease. In PET/CT studies, the operation can be done in the CT image space, and subsequently information is transformed to the PET space. If the anatomic image is not available, a non-attenuation corrected (NAC) PET can be reconstructed first and the user then defines the lesion proxies on the NAC PET images using the GUI. Position sensing physical devices (not shown) can also be used to place the lesion proxies in real physical space while the patient is on the couch before or after the PET acquisition. The clinician can define virtual lesions without actually place any activities at the locations, or can use external fiducials to serve the same purpose, as long as their characteristics can be controlled and known to the reconstruction processor 108.

The event simulation module 104 takes the specifications of the lesion proxies and simulates radioactive decay and annihilation events therefor. The simulation is scaled to the acquisition time span and reflects the actual time spent on each bed acquisition. The simulation uses the actual geometry and imaging characteristics of the detection systems, such as bore size, detector arrangement, dead time behavior, dead pixels, crystal efficiency and geometry normalization, etc. When the anatomic image such as CT or MR is available, photon attenuation and scattering are simulated. In short, the simulation faithfully reflects the actual imaging chain and system behavior. The simulated list mode and/or sinogram data is separable from the actual patient acquisition list mode or sinogram data acquired by the PET scanner 106. For reconstruction processing, however, the actual acquisition and simulated data are merged.

The modified reconstruction processor 108 monitors the image characteristics of the lesion proxies and dynamically adjusts the reconstruction and processing parameters. In a reconstruction example, since the position and size of the lesion proxies are known, lesion proxies can be segmented out on the intermediately reconstructed images. For instance, if a lesion proxy with a uniform activity distribution is placed in the patient image, during PET reconstruction, the intensity or SUV within the lesion proxy is monitored along with its uniformity index, noise level, etc. By monitoring these attributes, the iterative reconstruction algorithm can dynamically adjust the number of iterations, in addition to other parameters (e.g., proxy size, shape, type, density, position, etc.). When the iteration number is small, the image is not convergent yet. The image might be overly smooth and its value might be far away from the truth. When the iteration number is large, the noise level of the image becomes high. This is the typical bias-variance trade-off. Conventional monitoring without the herein-described lesion proxies is difficult, since there is no known ground truth.

Additionally, if the reconstruction algorithm detects, with a current parameter setting, that a desirable image quality and quantitation targets will not be achieved, the reconstruction processor can choose a different set of parameters (such as number of subsets), or a totally different reconstruction algorithm. It is also possible to search the parameter space to find an optimal set of parameters to achieve the specified image quality and quantitation targets.

In a post-processing example, a post-processing filtering algorithm 118 such as one based on PSF (point spread function) is employed, e.g., by a processor 120. The filtering algorithm has adjustable parameters. By measuring and monitoring the image quality and quantitation on the lesion proxies, the filtering parameters can be adjusted to achieve the image quality and quantitation targets, being it image resolution, noise level, SUV accuracy, variation, etc.

Additionally, there are multiple ways to search the parameter space to find the optimal parameters. If the parameter space is low-dimensional, exhaustive search can be performed. That is, different points in the parameter space are tried and the best identified parameter(s) is/are kept until all possible permutations have been evaluated. When the parameter space is high dimensional and it is prohibitive to do exhaustive search, any optimization algorithms can be employed, e.g. Simplex algorithm or Powell's conjugate direction search.

The described systems and methods can be used during image review, e.g., by a physician. For example, if the physician desires to interrogate a lesion spotted during image review, he can place a few lesion proxies surrounding the lesion. The reconstruction processor reconstructs the image again, using the previous set of parameters. By analyzing the image attributes of the lesion proxies, the physician can improve his confidence on diagnosis of the actual (real) lesion. For example, if all lesion proxies report a SUV close to their expected ground truth, the physician is confident as to the SUV measurement of the real lesion; on the other hand, if the lesion proxies report a SUV far away from the truth, the physician's confidence as to the measured SUV of the real lesion is reduced.

The statistic reporting tool 114 collects and reports image characteristics of the lesion proxies. As the lesion proxies were introduced with known properties (e.g., by a clinician), they can be segmented out and the calculation of the reconstructed lesion proxies can be readily performed. These characteristics include, but are not limited to, image resolutions in different directions, geometric properties such as size (e.g. volume, dimension in each direction) and shape (e.g. roundness), SUV max/mean/min, uniformity, SUV accuracy, etc. Differences as compared to the proxies' respective ground truths are conveniently calculated and reported, and stored in a memory 122 as statistical data 124. The statistics of the lesion proxies can be reported individually or collectively to provide reference for physicians to make a diagnostic decision during reading.

The inpainting tool 116 removes the lesion proxies from the patient image when the proxies are no longer desired or needed. Since the lesion proxies are introduced for image quality and quantitation monitoring and optimization, they can be removed from the final reconstructed or processed images before they are sent out for review by clinicians. In one embodiment, the user has the option to preserve the images with lesion proxies. In another embodiment, a lesion proxy "toggle" 126 is provided via the GUI 102 to permit a viewer to toggle between images with lesion proxies 128 and images without lesion proxies 130, which are also stored in the memory 122. In another embodiment, when lesion proxies are shown in a given image, they are designated as such (e.g., via color-coding, highlighting, labeling, or any other suitable manner of designation) in order to mitigate confusion between lesion proxies and real image data. That is, when the lesion proxy toggle is "on," the lesion proxies are in a highlighted state (i.e., labeled, color coded, highlighted, etc.) to clearly delineate them from real image data. That is, when the lesion proxy toggle is "off," the lesion proxies are in a non-highlighted state in which they are not indicated to be different from real image data.

Because the lesion proxies are introduced with known location, shape, and size, they can be segmented out by using the same information. Such information is used to guide a segmentation algorithm, and the segmented volume may be slightly larger than the actual size of lesion proxies. Once the lesion proxies are segmented out, the image inpainting tool 116 replaces image values (voxels) at the location(s) of the lesion proxies. In one embodiment, a differential equation-based inpainting algorithm evaluates the properties surrounding the lesion proxies and propagates or interpolates those properties to replace the lesion proxy voxels.

It will be understood that the processor 120 executes, and the memory 122 stores, computer executable instructions for carrying out the various functions and/or methods described herein. The memory 122 may be a computer-readable medium on which a control program is stored, such as a disk, hard drive, or the like. Common forms of computer-readable media include, for example, floppy disks, flexible disks, hard disks, magnetic tape, or any other magnetic storage medium, CD-ROM, DVD, or any other optical medium, RAM, ROM, PROM, EPROM, FLASH-EPROM, variants thereof, other memory chip or cartridge, or any other tangible medium from which the processor 120 can read and execute. In this context, the described systems may be implemented on or as one or more general purpose computers, special purpose computer(s), a programmed microprocessor or microcontroller and peripheral integrated circuit elements, an ASIC or other integrated circuit, a digital signal processor, a hardwired electronic or logic circuit such as a discrete element circuit, a programmable logic device such as a PLD, PLA, FPGA, Graphics processing unit (GPU), or PAL, or the like.

Figure 3:
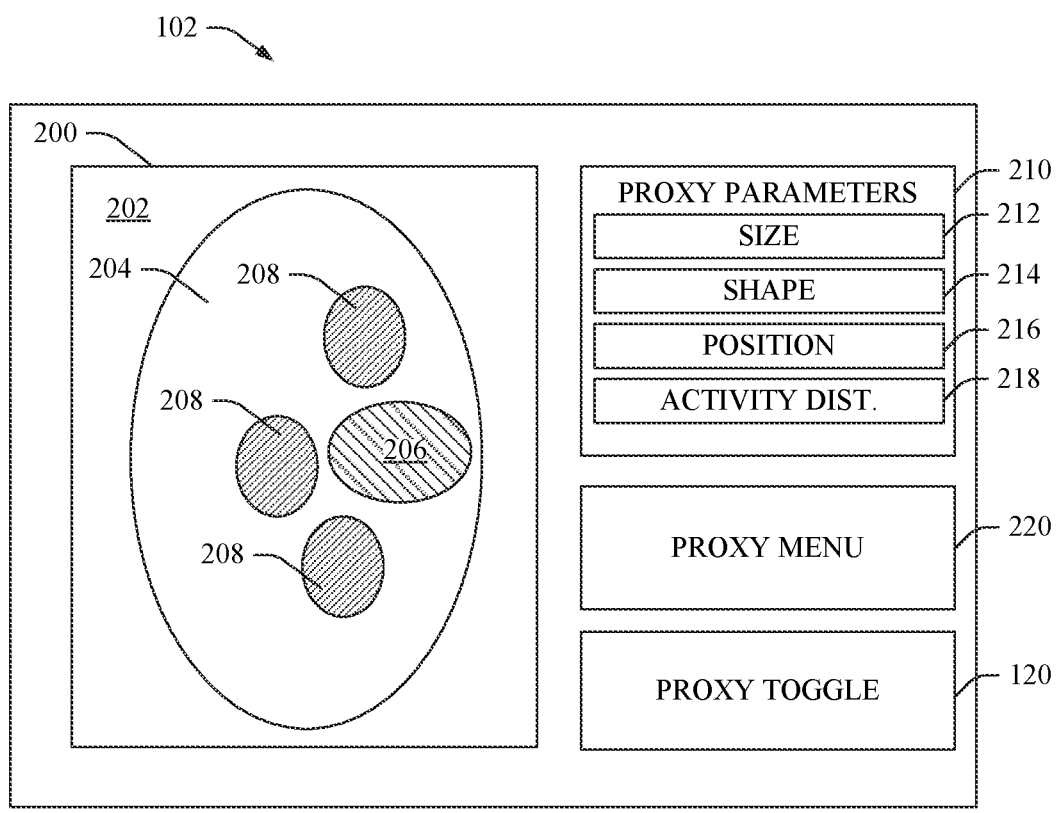
FIG. 3 is an illustration of a graphical user interface (GUI) that facilitates reconstructing a nuclear medicine image using lesion proxies, in accordance with one or more features described herein.

FIG. 3 is an illustration of a graphical user interface (GUI) 102 that facilitates reconstructing a nuclear medicine image using lesion proxies, in accordance with one or more features described herein. The GUI includes one or more image panels or region 200 in which patient images 202 are presented to a user. The patient image includes a region of interest (ROI) 204 with a real lesion 206. The user positions one or more lesion proxies 208 (e.g., artificial lesions) in the patient image. Although depicted within the ROI in FIG. 3, the lesion proxies 208 may also be placed outside the patient or ROI. The GUI also comprises a plurality of selectable and adjustable lesion proxy parameters 210, including a proxy position parameter tab 212, a size parameter tab 214, a shape parameter tab 216, and a radioactive activity distribution parameter tab 218, etc. In one embodiment, lesion proxy placement is performed using a drag-and-drop technique. Additionally, the GUI comprises a proxy toggle tab 120, which the user can select to toggle between a patient image comprising the lesion proxies and one that does not include the lesion proxies. In another embodiment, the toggle tab causes the image panel to switch between an image in which the lesion proxies are highlighted and one in which they are not.

In another embodiment, lesion proxies are selectable e.g., via a menu 220 or the like, and have a predefined shape, size, and radioactive activity distribution. For instance, each lesion proxy can be associated with a proxy ID that indicates its size, shape, and activity distribution. A user can open the proxy menu, select the desired proxy, and drag it onto the patient image to the desired location.

In yet another embodiment, the lesion proxies can be specified through a text file. For instance, a text file for a given lesion proxy can include data describing one or more parameters (e.g., size, shape, density, etc.) of the given lesion proxy.

It will be appreciated by those of skill in the art that the foregoing example(s) is/are not limited to the specific number and/or types of proxy parameters, etc., but rather any desired number and/or types of proxy parameters may be employed in conjunction with the systems and methods described herein.

It further will be appreciated that although the herein-described systems and methods are described with regard to providing proxies for lesions, the described systems and methods are not limited thereto and be employed to facilitate providing proxies for any suitable structure or object when reconstructing images.

The innovation has been described with reference to several embodiments. Modifications and alterations may occur to others upon reading and understanding the preceding detailed description. It is intended that the innovation be construed as including all such modifications and alterations insofar as they come within the scope of the appended claims or the equivalents thereof.

The invention claimed is:

1. A system that facilitates reconstructing a nuclear medicine image using lesion proxies, comprising:
   a PET scanner configured to acquire scan data of the patient;
   a graphical user interface (GUI) configured to receive parameter information describing one or more lesion proxies for positioning in a nuclear medicine image of a patient;
   an event simulation module configured to simulate the radioactive decay of the one or more lesion proxies;
   a reconstruction processor configured to merge lesion proxy simulation data with the acquired scan data, monitor image attributes of lesion proxies, adjust one or more reconstruction parameters as a function of lesion proxy status, and iteratively reconstruct the nuclear medicine image using one or more adjusted reconstruction parameters;
   wherein each iteration of the reconstructed nuclear medicine image is displayed on the GUI.

2. The system according to claim 1, wherein the monitored image attributes of the lesion proxies include a standardized uptake value (SUV) that is compared to a known SUV for the lesion proxies until a match is achieved, at which time reconstruction iteration is terminated.

3. The system according to claim 1, wherein the parameter information comprises one or more of a location, shape, size, and radioactive activity distribution for each of the one or more lesion proxies.

4. The system according to claim 1, further comprising a statistical reporting tool configured to calculate and report image characteristics of the one or more lesion proxies after reconstruction is complete.

5. The system according to claim 1, further comprising a statistical reporting tool configured to calculate and report image characteristics of the one or more lesion proxies after N iterations of image reconstruction, where N is an integer.

6. The system according to claim 1, further comprising a digital inpainting tool configured to segment out the lesion proxies and replace them with interpolated voxels upon a determination that reconstruction parameters are optimized.

7. The system according to claim 1, wherein the GUI further comprises a selectable proxy toggle option via which image data associated with the lesion proxies is toggled on or off.

8. The system according to claim 1, wherein the GUI further comprises a selectable proxy toggle option via which image data associated with the lesion proxies is toggled between a highlighted state and a non-highlighted state.

9. The system according to claim 1, wherein the one or more lesion proxies has at least one of a predefined size and a predefined shape.

10. The system according to claim 1, further comprising:
a computer-readable medium on which is stored, upon receipt of a signal indicating that the lesion proxy image quality is acceptable, a final image;
wherein the reconstruction processor is configured to stop iterating the reconstruction upon receipt of the signal indicating that the lesion proxy image quality is acceptable.

11. The system according to claim 10, wherein the final image is stored with statistical data describing the reconstruction parameters used to generate the final image.

12. The system according to claim 11, wherein the reconstruction processor is configured to generate a clean final image without the one or more lesion proxies by reconstructing the patient scan data using the reconstruction parameters described by the statistical data.

* * * * *